(12) United States Patent
Danz et al.

(10) Patent No.: US 7,603,162 B2
(45) Date of Patent: Oct. 13, 2009

(54) IMAGING TOMOGRAPHY APPARATUS WITH FLUID-CONTAINING CHAMBERS FORMING OUT-OF-BALANCE COMPENSATING WEIGHTS FOR A ROTATING PART

(75) Inventors: Günter Danz, Groß-Zimmern (DE); Hans-Jürgen Müller, Pretzfeld (DE)

(73) Assignee: Siemens Aktiengesellschaft, Munich (DE)

( * ) Notice: Subject to any disclaimer, the term of this patent is extended or adjusted under 35 U.S.C. 154(b) by 509 days.

(21) Appl. No.: 11/045,891

(22) Filed: Jan. 28, 2005

(65) Prior Publication Data

US 2005/0199058 A1   Sep. 15, 2005

(30) Foreign Application Priority Data

Jan. 28, 2004   (DE)   ................. 10 2004 004 297

(51) Int. Cl.
   *A61B 5/00*   (2006.01)
(52) U.S. Cl. ..................... 600/425; 73/460; 73/469; 378/4; 378/162; 600/437
(58) Field of Classification Search ......... 600/407–480; 73/460, 468, 462, 470, 457, 458; 378/119–144, 378/4–20, 207, 205; 250/363.04–363.1; 494/1, 10
   See application file for complete search history.

(56) References Cited

U.S. PATENT DOCUMENTS

| | | | |
|---|---|---|---|
| 4,002,086 A * | 1/1977 | Reinhall | 74/573.11 |
| 5,201,586 A | 4/1993 | Zimmermann et al. | |
| 5,354,186 A * | 10/1994 | Murtuza et al. | 417/474 |
| 6,189,372 B1 | 2/2001 | Danz | |
| 6,210,099 B1 | 4/2001 | Hugbart et al. | |
| 6,250,155 B1 | 6/2001 | Hormann et al. | |
| 6,276,145 B1 * | 8/2001 | Sharpless et al. | 62/51.1 |
| 6,354,151 B1 | 3/2002 | Freyermuth et al. | |
| 6,412,345 B1 * | 7/2002 | Murray et al. | 73/468 |
| 6,590,960 B2 * | 7/2003 | Kroener et al. | 378/162 |
| 7,020,233 B1 * | 3/2006 | Tybinkowski et al. | 378/4 |
| 2002/0114424 A1 * | 8/2002 | Kroener et al. | 378/4 |
| 2003/0159508 A1 | 8/2003 | Halsmer | |

FOREIGN PATENT DOCUMENTS

| | | |
|---|---|---|
| DE | 28 52 376 | 7/1980 |
| DE | 32 48 085 | 7/1986 |
| DE | 297 09 273 | 9/1997 |
| DE | 197 29 172 | 7/1998 |

(Continued)

*Primary Examiner*—Ruth S Smith
*Assistant Examiner*—Nasir Shahrestani
(74) *Attorney, Agent, or Firm*—Schiff Hardin LLP

(57) ABSTRACT

An imaging tomography apparatus, in particular an x-ray tomography apparatus or an ultrasound tomography apparatus, has a stationary unit with a sensor for measurement of an out-of-balance condition of an annular data acquisition device rotatable around a patient opening in the stationary device. Compensation weights for compensation of the out-of-balance condition are provided on the data acquisition device. To simplify the balancing procedure, the compensation weights are disposed in two parallel planes axially separated from one another, and in each plane at least three compensation weights are fashioned as chambers that can be filled with a fluid. At least two of the chambers are connected with one another via at least one conduit for fluid transfer therebetween exchange.

11 Claims, 2 Drawing Sheets

FOREIGN PATENT DOCUMENTS

| | | |
|---|---|---|
| DE | 197 43 577 | 4/1999 |
| DE | 299 13 630 | 4/2000 |
| DE | 199 20 698 | 12/2000 |
| DE | 199 20 699 | 10/2001 |
| WO | WO 2004/098413 | 11/2004 |

* cited by examiner

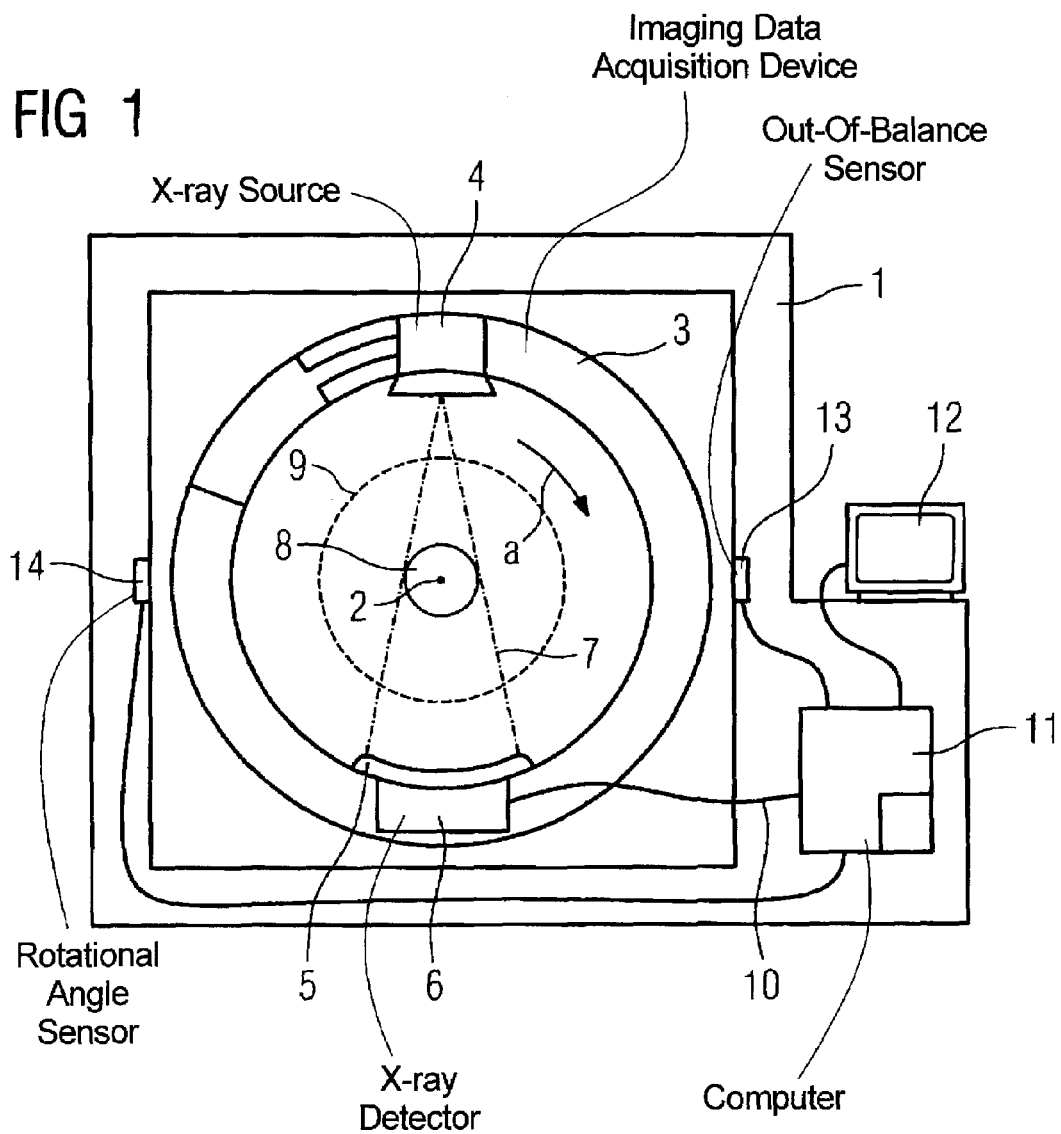

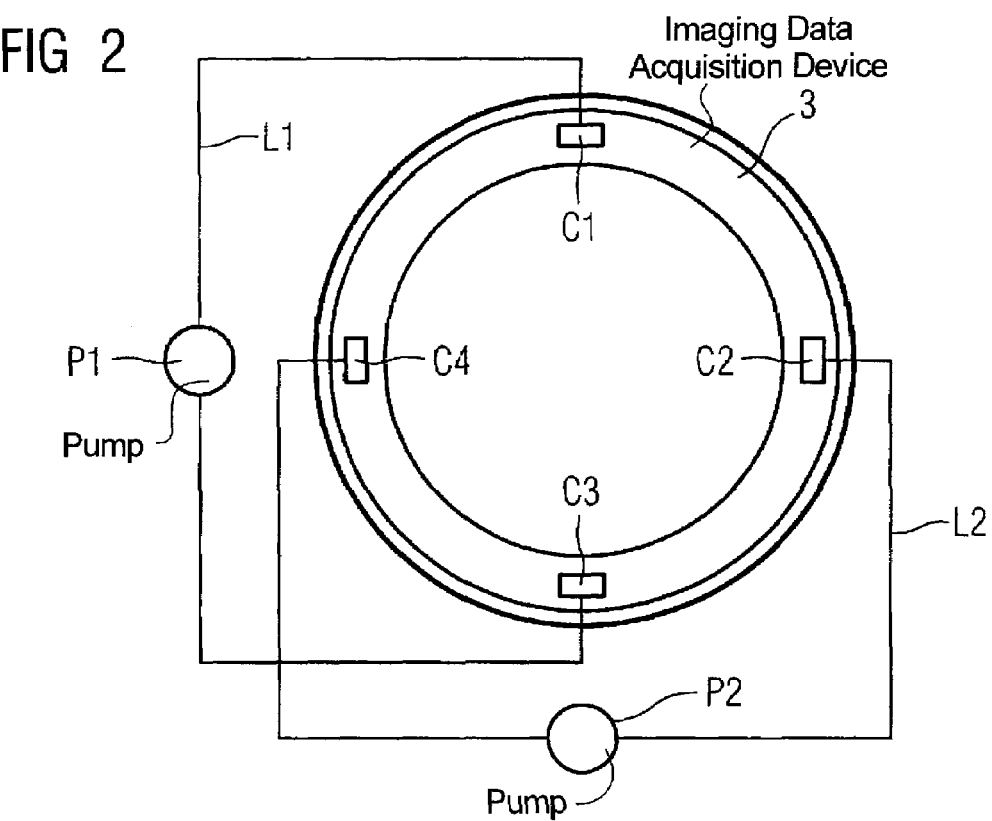
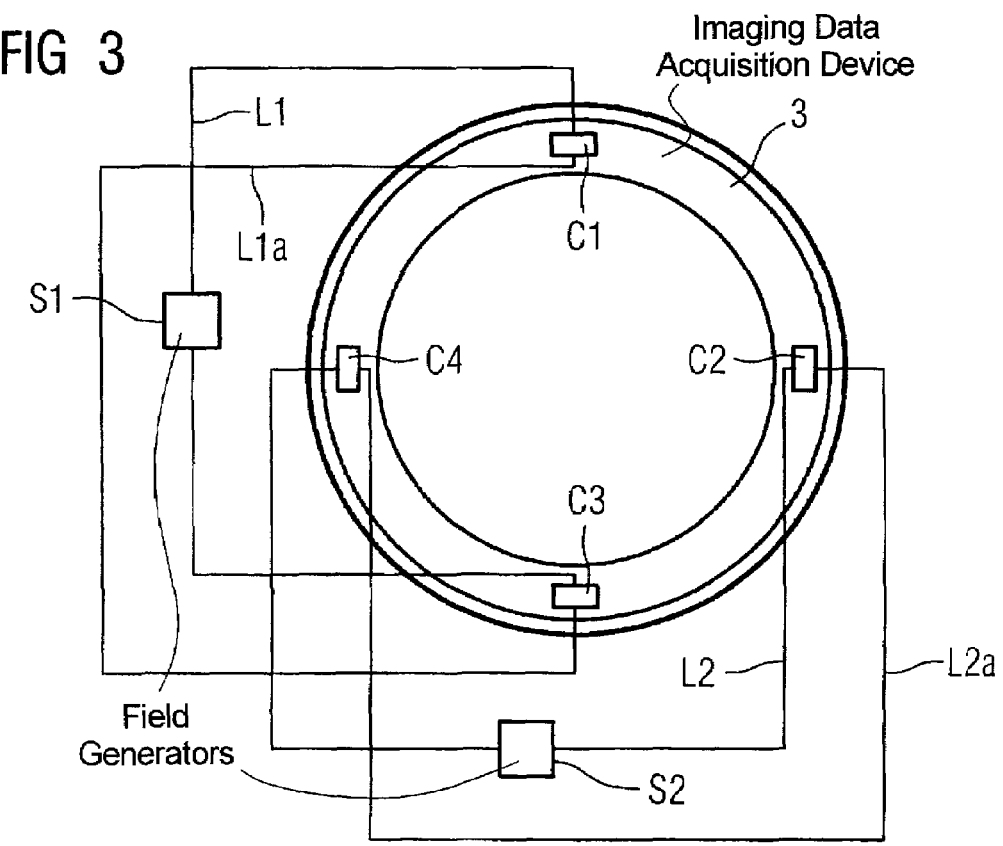

IMAGING TOMOGRAPHY APPARATUS WITH FLUID-CONTAINING CHAMBERS FORMING OUT-OF-BALANCE COMPENSATING WEIGHTS FOR A ROTATING PART

BACKGROUND OF THE INVENTION

1. Field of the Invention

The invention concerns an imaging tomography apparatus, in particular an x-ray computed tomography apparatus.

2. Description of the Prior Art

An x-ray computed tomography apparatus is known from German OS 101 08 065. A data acquisition device or gantry, mounted such that it can be rotated around a horizontal rotational axis, is accommodated in a stationary mount. A sensor to detect an out-of-balance (unbalanced) condition of the data acquisition device is provided on the stationary mount. The sensor is connected with a device to calculate the position or positions of the rotatable data acquisition device at which a compensation weight or weights should be applied to compensate the out-of-balance condition. The balancing can ensue without the use of a specific balancing device, but a trained person is required to implement the balancing procedure, in particular for correct application of the compensation weights. The balancing procedure requires, among other things, a partial demounting of parts of the x-ray computed tomography apparatus. This procedure thus is time-consuming and expensive.

U.S. Pat. No. 6,354,151 as well as German Translation 698 04 817 T2 describes an apparatus for balancing of an instrument mounting. The mass of the instrument mounting and its out-of-balance condition are thereby determined.

German Utility Model 297 09 273 discloses a balancing device for balancing rotors. Two compensation rings with a defined out-of-balance condition are provided that can be attached to one another on the rotor at suitable relative positions for compensation of an out-of-balance condition of the rotor.

German PS 199 20 699 also discloses a method for balancing rotors. Two compensation rings respectively exhibiting a defined out-of-balance condition are mounted on the rotor. To compensate the out-of-balance condition, the relative positions of the compensation rings relative to one another can be changed. For this purpose, an attachment device of the compensation rings is released. The compensation rings are held by a pawl and the rotor is rotated by a predetermined angle relative to the compensation rings. The compensation rings are subsequently locked (arrested).

To ease the locking of such compensation rings, in German OS 199 20 698 it is disclosed to fix the rings in their relative positions by means of a spring-loaded locking device on the rotor. By means of an applied force, the compensation rings can be displaced in their relative positions relative to the rotor and naturally can be locked.

To ease the identification of the correct locking position of such compensation rings, in German Utility Model 298 23 562 discloses projecting markings onto the compensation elements by means of a marking device when the rotor is located in a compensation position.

German PS 197 29 172 discloses a method for continuous compensation of an out-of-balance rotor. The out-of-balance condition of the rotor is measured by means of an out-of-balance measurement device. For compensation of the out-of-balance condition, the rotor has a number of compensation chambers filled with compensation fluid and disposed at different relative rotor positions. To compensate the out-of-balance condition, the quantity of the compensation fluid in the compensation chambers is increased or reduced in a suitable manner.

German Utility Model 299 13 630 concerns an apparatus for compensation of an out-of-balance condition in a machine tool or balancing machine. The balancing machine is thereby balanced using counterweight rotors and the position of the counterweight rotors is stored. The balancing machine is subsequently re-balanced with a component incorporated therein by displacement of the counterweight rotors. The out-of-balance condition of the component can be inferred from the deviating position of the counterweight rotors without and with the component.

German OS 197 43 577 and German OS 197 43 578 disclose a method for balancing a rotating body. Compensation masses that can be radially displaced and/or displaced in terms of their relative positions with respect to the rotating body are attached to the rotating body. At the beginning of the method, the compensation masses are initially brought into a zero position in which the vectors generated by them mutually cancel. The out-of-balance condition of the rotating body is subsequently measured and compensated by suitable shifting of the compensation masses.

The implementation of these known methods typically requires technically trained personnel. Independently of this, some of the known methods are not suited for balancing of a measurement device of a tomography apparatus.

SUMMARY OF THE INVENTION

An object of the present invention is to remedy the aforementioned disadvantages according to the prior art. In particular, an imaging tomography apparatus should be provided having a rotatable measurement device that can be optimally simply balanced. The balancing procedure should be fully automatically implementable, such that trained personnel are not required.

The object is achieved according to the invention by an imaging tomography apparatus having an annular, rotatable data acquisition device with the compensation weights in two parallel planes that are axially separated from one another, and wherein each plane at least three compensation weights are fashioned as chambers that can be filled with a fluid. At least two of the chambers are connected with one another via at least one conduit for fluid transfer therebetween. The degree of filling of the respective chambers compensates for a detected out-of-balance condition of the data acquisition device.

The out-of-balance condition may be detected by a server on the stationary unit in which the data acquisition device is rotatably mounted, which detects vibrations transferred to the stationary unit due to the out-of-balance condition of the data acquisition device.

Because the compensation weights are disposed in two parallel planes that are axially separated from one another, compensation of an out-of-balance condition caused by a non-uniform axial weight distribution is also possible. Wobbling movements thus can be compensated with this arrangement. Because at least two of the chambers in a plane are connected with at least one conduit, a compensation weight necessary for compensation of an out-of-balance condition can be adjusted in a simple manner by fluid transfer. The inventive arrangement can be controlled particularly simply. It is also possible for both of the opposite chambers to be connected with one another by means of two conduits. By a suitable connection of both conduits, centrifugal forces acting on the fluid can be compensated.

In an embodiment, a pump is connected in the conduit. This enables a back-and-forth pumping of fluid from one chamber into another.

A magnetic fluid can be used as the aforementioned fluid. A magnetic fluid is a fluid whose viscosity changes under the influence of a magnetic field. Given the use of a magnetic fluid as the fluid, the pump can be a device for generation of an electrical or magnetic field penetrating the conduit section-by-section. Magnetic fluid can be bumped back and forth by a suitable change of the electrical or magnetic field.

According to a further embodiment, a further sensor is provided to determine the rotation angle of the data acquisition device with regard to the stationary unit. This enables a particularly simple determination of the distribution of the compensation weights on the data acquisition device necessary for compensation of the out-of-balance condition.

According to a further embodiment, a control device controls the pump according to a predetermined algorithm for compensation of the out-of-balance condition of the data acquisition device. Such a control device can be, for example, a conventional controller with a microprocessor. The control device appropriately calculates a distribution of the compensation weights on the data acquisition device necessary for compensation of the out-of-balance condition, dependent on the signals provided by the sensor means for measurement of the out-of-balance vibration as well as, if applicable, dependent on the further sensor for determination of the rotational angle of the data acquisition device. Dependent on the measurement result, the pump is controlled such that a fluid movement necessary to achieve the calculated compensation weight distribution occurs in the chambers.

DESCRIPTION OF THE DRAWINGS

FIG. 1 is a schematic side view of a tomography apparatus.

FIG. 2 is a schematic side view of a first embodiment of a data acquisition device according to the invention.

FIG. 3 is a schematic side view of a second embodiment of a data acquisition device according to the invention.

DESCRIPTION OF THE PREFERRED EMBODIMENTS

FIG. 1 schematically shows a side view of an x-ray tomography apparatus with a stationary unit 1. An annular imaging data acquisition device 3 (gantry) is accommodated on the stationary unit 1 such that it can rotate around a rotation axis 2 disposed at a right angle to the plane of the drawing. The rotation direction of the imaging data acquisition device 3 is designated with the arrow a. An x-ray source 4 and an x-ray detector 5 with downstream evaluation electronic 6 are mounted on the imaging data acquisition device 3 opposite to each other. A beam fan 7 radiated by the x-ray source 4 defines a circular measurement field 8 given a rotation of the imaging data acquisition device 3. The measurement field 8 is located within a patient opening 9 indicated with the dashed line. The evaluation electronic 6 is connected with a computer 11 via a slip ring contact 10 (indicated schematically). The computer 11 has a monitor 12 for display of data. A sensor 13 for measurement of vibrations transferred to the stationary unit 1 is provided on the stationary unit 1. This is a conventional sensor with which vibrations caused by an out-of-balance condition of the imaging data acquisition device 3 and transferred to the stationary unit 1 can be measured in the radial direction and the axial direction. A further sensor 14 attached to the stationary unit 1 serves for the detection of the rotational angle of the imaging data acquisition device 3 relative to the stationary unit 1. The sensor 13 and the further sensor 14 are likewise connected with the computer 11 for evaluation of the signals measured therewith. In FIG. 1, for clarity compensation weights provided on the data acquisition device 3 are not shown.

In the schematic side views of the respective embodiments of the data acquisition device 3 in FIGS. 2 and 3, for clarity the x-ray source 4 and the x-ray detector 5 with downstream evaluation electronic 6 are not shown. Four chambers C1, C2, C3 and C4 with an offset of 90° are attached to the data acquisition device 3 in a plane. Two pairs of opposing chambers C1, C3 and C2, C4 are provided. In the embodiment of FIG. 2, the chambers C1, C3 are connected with one another by a conduit L1 for fluid exchange therebetween. The chambers C2, C4 are connected by a conduit L2 for fluid exchange therebetween. Respective pumps P1, P2 are connected in the conduits L1, L2. The two pairs of opposing chambers C1, C3 and C2, C4, the conduit L1 and L2 and the pumps P1 and P2 connected therein form a compensation weight whose "position" (angular momentum effect) can be modified via back-and-forth transfer of fluid relative to the data acquisition device 3. The fluid can be, for example, hydraulic fluid.

In the second embodiment shown in FIG. 3, the chambers in the opposing pairs of chambers C1, C3 and C2, C4 are connected via two conduits. Conduit L1 connects a radially outward port of chamber C1 to a radially inward port of chamber C3. Conduit L1a connects a radially inward port of chamber C1 to a radially outward port of Chamber C3. Conduits L2 and L2a provide similar connections between chambers C2 and C4. Centrifugal forces that act on the fluids housed in the chambers C1, C2, C3, C4 can be compensated by the conduits L1, L1a, L2, L2a. As a result, only a small capacity is necessary for back-and-forth pumping of fluid between the chambers during the rotation of the data acquisition device 3. In this embodiment, field generators S1, S2 for generation of a magnetic field or an electric penetrating the conduits L1, L2 in sections are provided instead of the pumps P1, P2. If a magnetic fluid is used as the fluid, the field generators S1, S2 are coils. A magnetic fluid is a fluid with magneto-rheological properties, i.e. the viscosity of the fluid is dependent on the strength of a magnetic field acting on it. For example, it becomes highly viscous or under the influence of a magnetic field. Thus by generation of a suitable magnetic field by means of the coils S1, S2 a flow of the magnetic fluid through the conduits L1, L2 can be produced. Instead of the magnetic fluid, a fluid with electro-rheological properties can be used whose viscosity is dependent on the strength of an electrical field acting on it. In this case, instead of coils, the field generators S1, S2 are electrodes for the generation of an electrical field penetrating the conduits L1, L2.

In each of FIGS. 2 and 3, the arrangement of the compensation weights is shown in a first plane. Such a first plane proceeds perpendicular to the rotation axis 2 and can be formed, for example, by the front side of the data acquisition device 3. In order to ensure a complete compensation of an out-of-balance condition of the data acquisition device 3, further compensation weights can be provided on the data acquisition device 3 in a second plane parallel to the first plane. The second plane can be, for example, a backside of the data acquisition device 3 opposite to the front side. The compensation device provided in the second plane can be fashioned corresponding to the compensation device shown in FIGS. 2 and 3 as well.

Although modifications and changes may be suggested by those skilled in the art, it is the intention of the inventors to embody within the patent warranted hereon all changes and modifications as reasonably and properly come within the scope of their contribution to the art.

We claim as our invention:

1. An imaging tomography apparatus comprising:
   a stationary unit having a patient opening therein;
   an imaging data acquisition device rotatably mounted in said stationary unit, said imaging data acquisition device rotating around an axis and around said patient opening, said data acquisition device having a structural configuration subject to simultaneously occurring axial imbalance and radial imbalance with respect to said axis; and
   in each of two parallel planes of said imaging data acquisition device, axially separated from each other, at least three chambers respectively containing fluid, with at least one conduit placing at least two of said at least three chambers in fluid communication allowing fluid exchange between said at least two of said at least three chambers to alter respective amounts of said fluid in said at least two of said at least three chambers, said at least three chambers in each of said two parallel planes, with said fluid therein, forming a compensation weight system that compensates an out-of-balance condition of said imaging data acquisition device, caused by both said axial imbalance and said radial imbalance, dependent on respective amounts of said fluid in said at least three chambers.

2. An imaging tomography apparatus as claimed in claim 1 wherein in each of said planes, four of said chambers are disposed offset from each other by approximately 90°, said chambers forming two pairs of oppositely-disposed chambers with the chambers in each pair being connected to each other by at least one conduit allowing fluid exchange between the chambers in that pair.

3. An imaging tomography apparatus as claimed in claim 1 comprising a mechanical pump in said at least one conduit that effects said fluid exchange.

4. An imaging tomography apparatus as claimed in claim 1 wherein said fluid is a fluid having a magneto-rheological property, and comprising a coil that generates a magnetic field that interacts with said fluid for effecting said fluid exchange.

5. An imaging tomography apparatus as claimed in claim 1 wherein said fluid is a fluid having an electro-rheological property, and comprising an electrode that generates an electric field that interacts with said fluid for effecting said fluid exchange.

6. An imaging tomography apparatus as claimed in claim 1 comprising a sensor at said stationary unit that detects said out-of-balance condition of said imaging data acquisition device.

7. An imaging tomography apparatus as claimed in claim 6 comprising a further sensor at said stationary unit that detects a rotational angle of said imaging data acquisition device.

8. An imaging tomography apparatus as claimed in claim 7 comprising an exchange element disposed to interact with said fluid in said at least one conduit for effecting said fluid exchange, and a control unit connected to said sensor, said further sensor and said fluid exchange unit, that controls said fluid exchange unit to effect said fluid exchange dependent on respective signals from said sensor and said further sensor.

9. An imaging tomography apparatus as claimed in claim 1 wherein said imaging data acquisition device is an x-ray tomography imaging data acquisition device.

10. An imaging tomography apparatus as claimed in claim 1 wherein said imaging data acquisition device is an ultrasound tomography imaging data acquisition device.

11. An imaging tomography apparatus comprising:
    a stationary unit having a patient opening therein;
    an imaging data acquisition device rotatably mounted in said stationary unit, said imaging data acquisition device rotating around an axis and around said patient opening, said data acquisition device having a structural configuration subject to simultaneously occurring axial imbalance and radial imbalance with repeat respect to said axis; and
    in each of two parallel planes of said imaging data acquisition device, axially separated from each other, at least three chambers respectively containing fluid, with at least one conduit placing at least two of said at least three chambers in fluid communication allowing fluid exchange between said at least two of said at least three chambers to alter respective amounts of said fluid in said at least two of said at least three chambers, said at least three chambers in each of said two parallel planes, with said fluid therein, forming a compensation weight system that compensates an out-of-balance condition of said imaging data acquisition device, cause by both said axial imbalance and said radial imbalance, dependent on respective amounts of said fluid in said at least three chambers;
    a sensing arrangement at said image acquisition device that emits at least one signal related to said out-of-balance conditioning; and
    a control unit in communication with said sensing arrangement to receive said at least one signal therefrom, said control unit being configured to control said fluid exchange to compensate said out-of-balance condition.

* * * * *